United States Patent [19]

Ezer et al.

[11] Patent Number: 4,691,017
[45] Date of Patent: Sep. 1, 1987

[54] 2-HYDROXY-AND 2-HALO-ETHYLTHIOPYRIDINE INTERMEDIATES FOR PREPARING ANTIULCER COMPOUNDS

[75] Inventors: Elemer Ezer; Kalman Harsanyi; Hajnalka Vikar née Pethó ; Judit Matuz; Laszló Szporny; Eszter Cholnoky; Osaba Kuthi; Ferenc Trischler; Bela Hegedus; Márta Kapolnás née Pap; Anna Kállay née Sohonyai, all of Budapest, Hungary

[73] Assignee: Richter Gedeon Vegyeszeti Gyar Rt., Budapest, Hungary

[21] Appl. No.: 912,999

[22] Filed: Sep. 26, 1986

Related U.S. Application Data

[63] Continuation-in-part of Ser. No. 783,842, Oct. 3, 1985, Pat. No. 4,624,959, and Ser. No. 783,875, Oct. 3, 1985.

[30] Foreign Application Priority Data

Oct. 5, 1984 [HU] Hungary .............................. 3777/84
Oct. 5, 1984 [HU] Hungary .............................. 3775/84

[51] Int. Cl.$^4$ .......................................... C07D 213/70
[52] U.S. Cl. .................................................... 546/298
[58] Field of Search ......................................... 546/298

[56] References Cited

PUBLICATIONS

Chem. Abstracts, vol. 96, 35097w, (Feb. 1, 1982).

*Primary Examiner*—Alan L. Rotman
*Assistant Examiner*—J. Richter
*Attorney, Agent, or Firm*—Karl F. Ross; Herbert Dubno

[57] ABSTRACT

New intermediate compounds of the formula (I) are disclosed

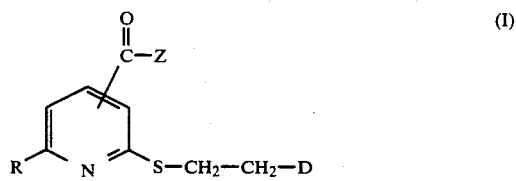

wherein
R is hydrogen or $C_1$ to $C_4$ alkyl;
Z is phenyl optionally substituted by one or more halogen atoms and/or alkyl groups having 1 to 4 carbon atoms; and
D is hydroxy, mesyloxy, p-tosyloxy, or halogen; or pharmaceutically acceptable acid addition salt thereof. The compounds of the Formula (I) are intermediates in the preparation of new compounds having anti-ulcer activity.

4 Claims, No Drawings

2-HYDROXY-AND 2-HALO-ETHYLTHIOPYRIDINE INTERMEDIATES FOR PREPARING ANTIULCER COMPOUNDS

CROSS REFERENCE TO RELATED APPLICATIONS

This application is a continuation-in-part of Ser. No. 783,842 now U.S. Pat. No. 4,624,959 filed Oct. 3, 1985 and Ser. No. 783,875 also filed Oct. 3, 1985, the contents of each being expressly incorporated herein by reference.

This invention relates to new pyridine derivatives. More particularly the invention concerns new pyridine derivatives of the Formula (I)

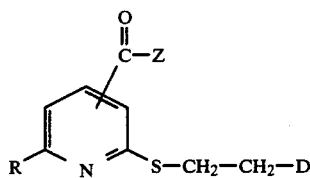

wherein
R is hydrogen or $C_1$ to $C_4$ alkyl;
Z is phenyl optionally substituted by one or more halogen atoms and/or alkyl groups having 1 to 4 carbon atoms; and
D is hydroxy, mesyloxy, p-tosyloxy, or halogen; or pharmaceutically acceptable acid addition salts thereof.

Preferably the —CO—Z substituent is bonded to the 3- or 4-position of the pyridine ring.

A preferred group of the Formula (I) compounds has the Formula (I')

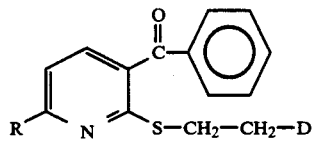

wherein R and D are each as defined above; or pharmaceutically acceptable acid addition salts thereof.

Preferred species within the scope of Formula (I) and (I') include:
3-benzoyl-2-[(2-hydroxy-ethyl)-thio-]pyridine; and
3-benzoyl-2-[(2-chloroethyl-thio]-pyridine; or a pharmaceutically acceptable acid addition salt thereof.

In the above formula in the definition of Z, the term $C_1$ to $C_4$ alkyl is used to refer to straight or branched alkyl groups, e.g. methyl, ethyl, n-propyl, isopropyl, n-butyl, isobutyl, sec-butyl, tert-butyl.

In the definition of Z in Formula (I) the phenyl group is preferably unsubstituted or carries 1 or 2 substituents. Preferred substituents are chloro or methyl.

The term halogen used throughout this specification refers to chlorine, fluorine, bromine or iodine, preferably chlorine or bromine.

In order to prepare compounds of the Formulae (I) or (I') either of the following methods may be used.

(a₁) a 2-halopyridine derivative of the Formula (II)

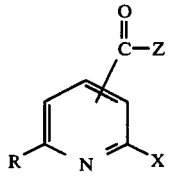

wherein X is halogen, is reacted with a thiol derivative of the Formula (III)

$$HS-CH_2-CH_2-D \qquad (II)$$

or an acid addition salt thereof; or (a₂) a pyridine-2-thione derivative of the Formula (IV)

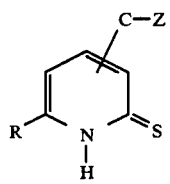

is reacted with a 2-haloethane derivative of the Formula (V)

$$X-CH_2-CH_2-D$$

or an acid addition salt thereof.

According to process (a₁) of the invention the compounds of formula (II) are reacted with the compounds of formula (III), wherein the substituents are as hereinbefore defined, in a solvent, preferably in the presence of an acid binding agent. As a solvent preferably lower alcohols having from 1 to 4 carbon atoms, water or a mixture thereof may be employed. Preferred acid binding agents are the alkali metal hydroxides, carbonates, alcoholates, or organic bases, such as triethyl amine or quaternary ammonium compounds. The reaction temperature may vary within a wide range, depending on the solvent employed and on possible side-reactions. It is preferred, however, to carry out the reaction between 25° C. and 80° C. in order to achieve an acceptable reaction velocity. By proper selection of the solvent it can be achieved that after termination of the reaction the inorganic salts may be filtered off. After evaporation of the reaction mixture the crystalline products may be purified by recrystallization, and the products, which cannot by crystallized in base form can be isolated from their aqueous solutions by extraction with water-immiscible organic solvents, such as chlorinated hydrocarbons, ethers or ethyl acetate and evaporation of the organic phase. If desired, the product can further be purified by distillation in vacuum. The products having poor crystallization properties in base form can be converted into corresponding, readily crystallizable acid addition salts, preferably hydrochlorides.

Process (a₁) according to the invention can be performed in an acidic medium, too. In this case the reactants are reacted preferably in a concentrated aqueous hydrochloric acid solution, at the boiling point of the reaction mixture.

In process (a₂) the reaction of the compounds of formula (IV) with the compounds of formula (V) is carried out essentially as described in connection with process (a₁), first variant, in the presence of a base.

The pharmaceutically acceptable acid addition salts of Formulae (I) and (I') include salts of mineral acids such as hydrochloric, hydroiodic, hydrobromic, phosphoric, metaphosphoric, nitric and sulfuric acids, as well as salts of organic acids including monobasic and dibasic carboxylic acids such as tartaric, acetic, citric, malic, benzoic, glycollic, gluconic, gulonic, succinic, and aryl sulfonic acids such as p-toluene-sulfonic acid.

Compounds of the formula (II) used as starting material in parocess variant (a₁) are partly known, thus some of them are described in the European patent application No. 80010027.2 published under No. 0032516, or can easily be prepared by known chemical reactions [Org. Synth. Coll. Vo. 4 88 (1963); Wolfenstein and Hartwich, Ber. 48, 2034 (1915)].

Compounds of the Formula (III) used in the process variant (a₁), compounds of the formula (V) used in process variant (a₂) are known, commercially available compounds or can easily be prepared from such substances.

The pyridine-2-thione derivatives of the Formula (IV) are either known (Spanish patent specifications Nos. 506,366, 506,367 and 506,368) or can be prepared from known, commercially available compounds by known methods.

Compounds of the formula (I) can be converted into their acid addition salts by reaction with the abovementioned suitable acids.

Salt formation can be carried out, for example, in an inert organic solvent, such as a C₁-6 aliphatic alcohol, by dissolving the compound of the formula (I) in the solvent and adding the selected acid or a solution thereof formed with the same solvent to the first solution until it becomes acidic. Thereafter the acid addition salt separates and can be removed from the reaction mixture e.g. by filtration.

The compounds of the Formula (I) and (I') are intermediates in the preparation of pharmaceutically active anti-ulcer pyridine derivatives of the Formula (VI)

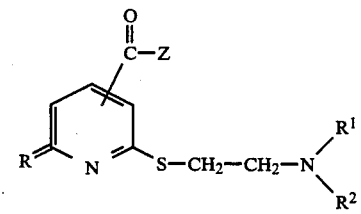

wherein R¹ and R² each independently represent hydrogen, alkyl having 1 to 4 carbon atoms, alkylphenyl having 1 to 4 carbon atoms in the alkyl moiety or an R—CO— group in which R is as defined above, and the —CO—Z substituent is preferably bonded to the pyridine ring in position 3 or 4, with the proviso that if R¹ and R² are both methyl, and Z is 4-chlorophenyl, then R is other than hydrogen, as well as pharmaceutically acceptable acid addition salts thereof as defined above.

The antiulcer compounds of the Formula (VI) may be prepared by (i) reacting a compound of the Formula (I'') falling within the scope of Formulae (I) or (I')

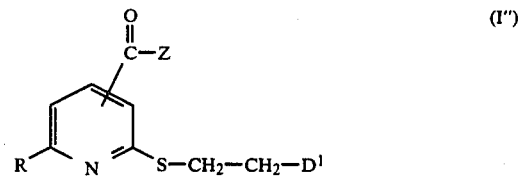

wherein D¹ is mesyloxy, p-tosyloxy, or halo; or an acid addition salt thereof, with an amine of the Formula (VII)

or (ii) to prepare compounds of the Formula (VI) where R¹ and R² are each hydrogen, reacting a 2-haloethylthio-pyridine of the Formula (I'') with phthalimide-K and eliminating the phthaloyl-protecting group in a manner known per se.

In process (i) the halide or the mesyloxy or p-tosyloxy ester of the Formula (I'') or an acid addition salt thereof is reacted with an excess amount of the amine of the Formula (VII) in an organic solvent, optionally under pressure. Of the compounds of the Formula (VII) preferably an excess of 2 to 5 moles is employed, and the reaction temperature is generally between 50° C. and 150° C. As a solvent, preferably alcohols, chlorinated organic solvents, or solvents of acid amide type, e.g. dimethylformamide can be used.

In process (ii) by which primary amines can be prepared of the Formula (VI), where R¹ and R² are each hydrogen, the reaction is carried out according to the Gabriel synthesis in an inert organic solvent, preferably dimethylformamide, preferably at a slightly elevated temperature. The phthaloyl-protecting group is preferably eliminated by hydrolysis in the presence of a base, which may for example be hydrazine or methylamine.

In order to convert the compounds of the Formula (I) or (I') where D is hydroxy to the compounds of the Formula (I) or (I') where D is halogen, that is to compounds of the Formula (I''), halogenating agents suitable for replacing the hydroxy group, e.g. thionyl chloride, may be employed. The reaction for example may be employed by starting from an acid addition salt of the hydroxyethyl compound, in an organic solvent, e.g. chloroform, benzene, acetonitrile, or in a dipolar aprotic solvent. Furthermore reactive esters of the Formula (I'') where D is mesyloxy or p-tosyloxy can be prepared from the above starting material where D is hydroxy by employing sulfonic acid chlorides, e.g. p-toluene-sulfonic acid chloride, or they can be converted into acid addition salts e.g. hydrochlorides.

The anti-ulcer compounds of the Formula (VI) are disclosed in the abovementioned copending Ser. No. 783,875 and may be orally administered to a mammalian subject for the treatment of ulcers.

The following data support the anti-ulcer activity of the compounds of the Formula (VI).

The pharmacological activity of the new compounds of the Formula (VI) has been investigated by the following methods:

Gastric necrosis induced by acidic ethanol
(cytoprotective activity)

Female RG-Wistar rats weighing 120 to 150 g. each were fasted for 24 hours. Water was given ad libitum. The compounds to be tested were administered orally, 30 minutes prior to the oral administration of a mixture of 1 ml. of concentrated hydrochloric acid and 50 ml. of absolute ethanol in a dose of 0.5 ml./100 g of body weight. One hour later the animals were killed by overdosing with ether. Stomachs were removed and opened along the major curvature. After cleaning the wet weight of the stomachs was determined, and the difference between the wet weight obtained and the wet weight of the stomachs of untreated (control) animals was calculated, in order to determine the degree of gastric oedema. The stomachs were then dried and the gastic lesions were observed visually. Lengths of lesions were measured in millimeters. (Derelanko and Long, Proc. Soc. Exp. Biol. and Med. 166, 394 (1981)), and the length of the average lesions per stomach was given. Degree of cytoprotection was expressed in % related to the control.

The statistical evaluation of the results was carried out by the Student test.

The results of the above test for a particularly preferred compound ("A") are summarized in Table 1, while Table 2 shows the $ED_{50}$-values of certain compounds of formula (VI) Test compounds:

A = 2-[(2-aminoethyl)-thio]-3-benzoyl-pyridine.HCl
B = 3-benzoyl-2-{[2-(N,N-diacetylamino)-ethyl]-thio}-pyridine
C = 2-[(2-aminoethyl)-thio]-3-(p-chlorobenzoyl)-pyridine.HCl
D = 2-[(2-aminoethyl)-thio]-3-(2,5-dimethylbenzoyl)-pyridine.HCl
E = 2-[(2-aminoethyl)-thio]-4-benzoyl-6-propyl-pyridine.2 HCl

TABLE 1

| | | Gastric necrosis induced by acidic methanol | | | |
|---|---|---|---|---|---|
| Pre-treatment | N | Dose (mg./kg.) p.o. | Oedema (mg.) | Inhibition (%) | Haemorrhagic injury (mm) | Inhibition (%) |
| acidic methanolic control | 25 | — | 379 ± 43 | — | 85 ± 15 | — |
| A | 8 | 0.05 | 307 ± 42 | 19 | 48 ± 19 | 45 |
| A | 10 | 0.1 | 209 ± 51 | 45$^x$ | 38 ± 18 | 56$^x$ |
| A | 12 | 1.0 | 72 ± 28 | 82$^{xx}$ | 5 ± 1.5 | 96$^{xx}$ |
| A | 12 | 10.0 | 22 ± 12 | 95$^{xx}$ | 6 ± 3 | 94$^{xx}$ |
| cimetidine | 8 | 25 | 441 ± 82 | — | 82 ± 21 | 2 |
| cimetidine | 8 | 100 | 301 ± 42 | 21 | 42 ± 13 | 46 |

$^x p < 0.05$ related to the control group treated with
$^{xx} p < 0.01$ acidic methanol

TABLE 2

| | The $ED_{50}$-value of certain compounds in the acidic methanol | |
|---|---|---|
| Test Compound | Gastric oedema inhibition $ED_{50}$(mg./kg.p.o.) | Haemorrhagic injury inhibition $ED_{50}$(mg./kg./p.o.) |
| A | 0.2 | 0.1 |
| B | 1.0 | 2.0 |
| C | 10.0 | 15.0 |
| D | 10.0 | 10.0 |
| E | 20.0 | 25.0 |

Gastric acid secretion inhibiting activity on Shay rats
(Gastroenterology, 5, 43-46 (1945))

Female H-Wistar rats weighing 120-150 g each were fasted for 24 hours. Water was added ad libitum. The pylorus of the animals was ligated under light ether narcosis. The test drugs were administered during the operation, partially orally, partially intraperitoneally. 4 hours after treatment the animals were killed by an overdose of ether. The stomach was excised and cut along the large curvature. The volume and the pH of the contents were determined and in each case the HCl production was determined by titration.

The results obtained are shown in Table 3.

TABLE 3

| Treatment | N | Dose (mg./kg.) | Secretion HCl/4 hours μmol/100 g body weight | Secretion HCl inhibition (%) |
|---|---|---|---|---|
| Control | 10 | — | 564 ± 42 | — |
| A | 5 | 5 p.o. | 357 ± 35 | 37 |
| A | 15 | 10 p.o. | 350 ± 38 | 38 |
| A | 15 | 20 p.o. | 372 ± 40 | 34 |
| A | 5 | 40 p.o. | 124 ± 27 | 70$^x$ |
| A | 5 | 6 i.p. | 505 ± 29 | 11 |
| A | 10 | 12 i.p. | 200 ± 30 | 65$^x$ |
| A | 5 | 25 i.p. | 0 | 100 |

$^x p < 0.01$ related to the control group $ED_{50}$:50 mg./kg.

Indomethacin-induced antral and intestinal ulceration

Female RG-Wistar rats weighing 120 to 150 g. each were fasted for 24 hours. Water was added ad libitum. The animals were then given access to food for one hour, and 30 minutes after the administration of the test compounds a 15-mg./kg. oral dose of indomethacin was administered. 24 hours after indomethacin treatment the animals were killed by overdose of ether. Stomachs and the entire intestine were removed, the stomachs were opened along the main curvature, and the total ulcerated area (ulceration index, mm$^2$) was determined.

To evaluate the development of intestinal ulcers the so-called inflation technique of Ezer and Szporny (J. Pharm. Pharmacol. 27, 866 (1975)) was employed. The tensile strength of the intestinal wall expressed in mmHg weakens gradually parallel with the progress of ulceration. The statistical evaluation was carried out by the Student test. The results obtained are set forth in Table 4.

TABLE 4

| | | | Intestinal ulcer | Antral ulcer | |
|---|---|---|---|---|---|
| Treatment | N | Dose (mg./kg.p.o.) | t.s 24 hours after indomethacin treatment (mmHg) | Ulceration index (mm$^2$/stomach) | Rats having no ulcer |
| Indomethacin-control | 50 | 15 + carrier | 147 ± 11 | 14.8 | 15 |
| Indomethacin + A | 15 | 15 ± 5 | 162 ± 14 | 18.9 | 3 |
| Indomethacin + A | 20 | 15 ± 25 | 198 ± 9$^x$ | 4.0$^x$ | 12$^x$ |
| Indomethacin + Pirenzepine | 20 | 15 ± 25 | 152 ± 8 | 12.0 | 5 |

TABLE 4-continued

| Treatment | N | Dose (mg./kg.p.o.) | Intestinal ulcer t.s 24 hours after indomethacin treatment (mmHg) | Antral ulcer Ulceration index (mm²/stomach) | Rats having no ulcer |
|---|---|---|---|---|---|
| Indomethacin + Cimetidine | 10 | 15 ± 50 | 161 ± 8 | 14.7 | 2 |

$^x p < 0.01$ related to the control treated with indomethacin
t.s.: tensile strength

Inhibition of aspirin-induced gastric ulceration

Female H. Wistar rats weighing 120 to 150 g each were fasted for 24 hours. Water was given ad libitum. The stomach ulcer was induced by oral administration of aspirin in a dose of 100 mg./kg. (in Tween 80 suspension). The test was given simultaneously with the administration of aspirin, orally. The animals were killed by overdose if ether, 4 hours after treatment. The stomach was excised and cut along the large curvature. The red-brownish erosions on the glandular surface were counted. When evaluating the test results, the number of ulcers per stomach and its proportion to the number of ulcers found in the stomachs of control animals (inhibition of ulceration) were determined. The results are shown in Table 5.

TABLE 5

| Treatment | N | Dose (mg./kg.p.o.) | Ulcer/Stomach | Inhibition (%) |
|---|---|---|---|---|
| Aspirin-control | 30 | 100 + carrier | 15.0 + 3.1 | — |
| Aspirin + A | 20 | 100 + 1 | 9.4 + 4.1 | 38 |
| Aspirin + A | 10 | 100 + 2 | 8.0 + 3.0 | 47$^x$ |
| Aspirin + A | 10 | 100 + 10 | 3.7 + 4.5 | 76$^x$ |

$^x ED_{50}$ 2.1 mg./kg.

From the test results obtained it can be concluded that the compounds of the Formula (VI) have gastrocytoprotective properties. For example in case of Compound A the gastric acid secretion inhibiting activity was observed only in an about 500-times higher dose, accordingly, the compound has a selective gastrocytoprotective activity. This activity is not eliminated by indomethacin pre-treatment, and therefore, should be a process indpendent from prostaglandins.

EXAMPLE 1

3Benzoyl-2-[(2-hydroxyethyl)-thio]-pyridine.HCl
{2-[(2-hydroxyethyl)-thio]-3-pyridinyl}-phenylmethanone.HCl 10.88 g. (0.05 moles) of 3 benzoyl-2-chloropyridine and 3.84 g. (0.055 moles) of 2-mercapto-ethanol are dissolved in 30 cm³ of ethanol. To the solution a solution of 2.2 g. (0.055 moles) of sodium hydroxide in 30 cm³ of ethanol is added, and the reaction mixture is boiled for 2.5 hours. Thereafter 0.78 g. (0.01 mole) of 2-mercaptoethanol is added to the mixture, which is boiled for further 1.5 hours. The inorganic salt is filtered off, the solution is evaporated, the residue is dissolved in water and extracted with 1,2-dichloroethane.

The organic phase is washed with 2n sodium hydroxide and then with water evaporated and converted into the corresponding hydrochloride with hydrochloric acid in ethyl acetate. The obtained 3-benzoyl-2-[(2-hydroxyethyl)-thio]-pyridine.HCl melts at 126° to 127° C.

Analysis for $C_{14}H_{13}NO_2S.HCl$ (295.78): Calculated: C%=56.85, N %=4.74, S %=10.84, Cl %=11.99; Found: C%=56.68, N%=4.68, S %=10.53, Cl %=11.63.

| IR spectrum (KBr) | 3360 | cm$^{-1}$ | —OH |
|---|---|---|---|
| | 3100 −2100 | cm$^{-1}$ | $-\overset{|}{\underset{|}{N}}{}^+H$ |
| | 1600 | cm$^{-1}$ | C=O |
| | 1600, 800, 758, 710 | cm$^{-1}$ | Ar |
| NMR spectrum (CDCl$_3$) | 3.6 ppm | t | —S—CH$_2$— |
| | 3.9 ppm | t | —O—CH$_2$— |
| | 7.4–7.8 ppm | m | phenyl ring and pyridine 5-H |
| | 8.0 ppm | 2xd | pyridine 4-H |
| | 8.8 ppm | 2xd | pyridine 6-H |
| | 9.5 ppm | x$_s$ | —OH and $\overset{|}{\underset{|}{N}}H^+$ |

We claim:

1. A compound of the Formula (I)

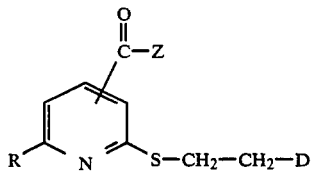
(I)

wherein
- R is hydrogen or C$_1$ to C$_4$ alkyl;
- Z is phenyl optionally substituted by one or more halogen atoms and/or alkyl groups having 1 to 4 carbon atoms; and
- D is hydroxy, mesyloxy, p-tosyloxy, or halogen; or a pharmaceutically acceptable acid addition salt thereof.

2. A compound of the Formula (I)

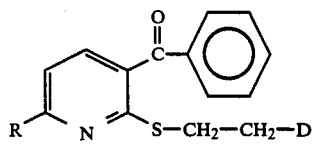
(I')

wherein
- R is hydrogen or C$_1$ to C$_4$ alkyl; and
- D is hydroxy, mesyloxy, p-tosyloxy, or halogen; or a pharmaceutically acceptable acid addition salt thereof.

3. 3-benzyl-2-[(2-hydroxyethyl)-thio]-pyridine as defined in claim 2 or a pharmaceutically acceptable acid addition salt thereof.

4. 3-benzyl-2-[(2-chloroethyl)-thio]-pyridine as defined in claim 2 or a pharmaceutically acceptable acid addition salt thereof.

* * * * *